(12) United States Patent
Witkowski et al.

(10) Patent No.: US 7,860,869 B2
(45) Date of Patent: *Dec. 28, 2010

(54) COMPUTER-IMPLEMENTED ELECTRONIC DIARY TO ENTER LOCKED LEGAL NOTES FOR HISTORICAL ARCHIVAL

(75) Inventors: Carl J. Witkowski, Duryea, PA (US); John H. Richardson, Wilkes-Barre, PA (US)

(73) Assignee: Guard Insurance Group, Wilkes-Barre, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/695,539

(22) Filed: Jan. 28, 2010

(65) Prior Publication Data

US 2010/0131511 A1  May 27, 2010

Related U.S. Application Data

(63) Continuation of application No. 11/164,730, filed on Dec. 2, 2005, now Pat. No. 7,668,828.

(51) Int. Cl.
*G06F 17/30* (2006.01)

(52) U.S. Cl. ............... 707/740; 705/311; 705/3; 705/4; 705/320; 705/38; 707/754

(58) Field of Classification Search ........... 707/740, 707/754, 6; 705/3–4, 30, 38, 311, 320; 715/230, 715/751
See application file for complete search history.

(56) References Cited

U.S. PATENT DOCUMENTS

| | | | |
|---|---|---|---|
| 5,535,322 A | 7/1996 | Hecht | |
| 5,623,681 A | 4/1997 | Rivette et al. | |
| 6,279,014 B1 | 8/2001 | Schilit et al. | |
| 6,487,569 B1 * | 11/2002 | Lui et al. | 715/230 |
| 6,546,405 B2 | 4/2003 | Gupta et al. | |
| 6,622,128 B1 * | 9/2003 | Bedell et al. | 705/30 |
| 7,392,484 B1 * | 6/2008 | Garfinkel et al. | 715/751 |
| 2002/0107713 A1 | 8/2002 | Hawkins | |
| 2003/0046282 A1 * | 3/2003 | Carlson et al. | 707/6 |
| 2003/0074229 A1 * | 4/2003 | Heise et al. | 705/4 |
| 2003/0120588 A1 * | 6/2003 | Dodd et al. | 705/38 |
| 2003/0187699 A1 | 10/2003 | Bonissone et al. | |
| 2003/0187700 A1 | 10/2003 | Bonissone et al. | |
| 2005/0010454 A1 * | 1/2005 | Falk et al. | 705/4 |
| 2005/0234888 A1 | 10/2005 | Bailey et al. | |

FOREIGN PATENT DOCUMENTS

| | | |
|---|---|---|
| JP | 62-88058 | 4/1987 |
| WO | WO 02/084520 | 10/2002 |

* cited by examiner

*Primary Examiner*—Don Wong
*Assistant Examiner*—Sheree N Brown
(74) *Attorney, Agent, or Firm*—IP Authority, LLC; Ramraj Soundararajan

(57) ABSTRACT

A system for the entry of legal notes, wherein the legal notes, after submission, are stored is non-editable form and are locked in a database for historical archival. In one scenario, the entered legal notes are editable and can be deleted for a pre-set time period, wherein, after the expiration of the pre-set time period, the entered legal notes are stored is non-editable form and are locked in a database for historical archival. Filters can be used to categorize and render the stored legal notes based on a set of categories.

6 Claims, 3 Drawing Sheets

Created: Alicia Noeer – 11/29/2005  08:34am     Category: Adjustor     [ edit ]  [ delete ]

Received call from DC stating that the insured has brought him back to work on Monday 11/28/2005 at a rate of $12.50 per hour for 35 hours a week. For his first week he will only work 25 hours.

FIG. 2

DocuNotes                                                                      printable view

| Category Filter: | ☐ No Category | ☐ Adjustor | ☐ Medical Management | ☐ Recovery |
|                  | ☐ SIU         | ☐ Supervisory | ☐ Payments        |           | add new entry filter

Created: Annette Stone – 04/21/2004  01:49pm            Category:  n/a

CLOSED CLAIM TODAY

Created: Annette Stone – 04/14/2004  04:24pm            Category:  n/a

There is a bill pending so the claim will not close. Will f/u in one wk on closure. The bill should have updated and paid by then.

FIG. 3

COMPUTER-IMPLEMENTED ELECTRONIC DIARY TO ENTER LOCKED LEGAL NOTES FOR HISTORICAL ARCHIVAL

RELATED APPLICATIONS

This application is a continuation of U.S. application Ser. No. 11/164,730 filed Dec. 2, 2005 now U.S. Pat. No. 7,668,828.

BACKGROUND OF THE INVENTION

1. Field of Invention

The present invention relates generally to an electronic diary. More specifically, the present invention is related to a computer-implemented electronic diary for entry of legal notes, wherein the legal notes, after submission, are stored is non-editable form and are locked in a database for historical archival.

2. Discussion of Prior Art

The following references generally describe the prior art, but none of the references cited below teach the entry of notes on an insurance policy or claim, wherein the notes, after submission, are stored is non-editable form and are locked in a database for historical archival. The following references also fail to teach or suggest the use of filters to categorize such notes, wherein the stored notes can be render based on a set of categories.

The patent to Schilit et al. (U.S. Pat. No. 6,279,014 B1), assigned to Xerox Corporation, provides for a system and method for extracting and organizing annotations made to a document on the basis of context and annotation attribute. The disclosed annotations are comprised of text, digital ink, audio, video, or any other input associated with a document.

The patent to Jones (WO 02/084520 A1), assigned to Pro-Super Holdings Limited, provides for a business tracking and communication system, wherein a business method is described for electronically handling claims, as well as underwriting policies. Also disclosed are user-edited notes that are inserted into an activities section of a policy.

The patent to Gupta et al. (U.S. Pat. No. 6,546,405 B2), assigned to Microsoft Corporation, provides for annotating temporally-dimensioned multimedia content. Disclosed is a system for annotating and displaying user-authored annotations in a multimedia document. Temporal annotations satisfying various are selected for inclusion into a multi-media document.

Whatever the precise merits, features, and advantages of the above cited references, none of them achieves or fulfills the purposes of the present invention.

SUMMARY OF THE INVENTION

The present invention provides for an article of manufacture having computer readable storage medium having instructions executable by a processor to implement an electronic diary for entry and category-based viewing of legal notes, wherein the method implemented by a processor comprises: executing instructions to receive legal notes input as formatted text; executing instructions to store the input legal notes in a database, wherein the stored text, after submission, are editable for a pre-determined time period and, after expiration of the pre-determined time period, the submission being non-editable and locked in the database for historical archival; executing instructions to implement one or more filters, each of the filters categorizing the stored legal notes based on a set of categories; executing instructions to receive inputs identifying at least one filter; executing instructions to filter the stored legal notes based on the identified at least one filter; and executing instructions to output categorized legal notes corresponding to the identified filters.

In one embodiment, the electronic diary is accessible over a network such as, but not limited to: a local area network, a wide area network, or the Internet.

The present invention also teaches a system comprising: a processor; and a computer readable storage medium having instructions executable by a processor to implement an electronic diary for entry and category-based viewing of legal notes, wherein the processor executes instructions to: receive legal notes input as formatted text; store the input legal notes in a database, wherein the stored text, after said submission, are editable for a pre-determined time period and, after expiration of the pre-determined time period, the submission is non-editable and is locked in the database for historical archival; implement one or more filters, each of the filters categorizing the stored legal notes based on a set of categories; receive inputs identifying at least one filter; filter said stored legal notes based on the identified at least one filter; and output categorized legal notes corresponding to the identified filters.

The present invention provides for a method comprising: receiving legal notes input as formatted text; storing said input legal notes in a database, wherein the stored text, after submission, are editable for a pre-determined time period and, after expiration of the pre-determined time period, the submission is non-editable and is locked in the database for historical archival; implementing one or more filters, each of said filters categorizing the stored legal notes based on a set of categories; receiving inputs identifying at least one filter; filtering the stored legal notes based on the identified at least one filter; and outputting categorized legal notes corresponding to the identified filters.

BRIEF DESCRIPTION OF THE DRAWINGS

FIGS. 1a-b illustrate an example of how a first note is added as per the present invention.

FIG. 2 illustrates the process of adding a new note according to the present invention.

FIG. 3 illustrates a non-exhaustive list of the various categories that a user can choose from.

DESCRIPTION OF THE PREFERRED EMBODIMENTS

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

The present invention provides for a computer-implemented electronic diary for entering notes on an insurance policy or claim, wherein the computer-implemented electronic diary comprises: a first component receiving submitted a note comprising formatted text regarding a insurance policy or claim; and a second component associating a category with the submitted note and storing the note in a database wherein the note, after said submission, is non-editable and is locked in said database for historical archival.

In an extended embodiment, the electronic diary of the present invention further comprises: a third component implementing one or more filters, wherein each of the filters categorizes said notes based on a set of categories; a fourth component receiving inputs identifying at least one filter, wherein the filter identifies at least one category; and a fifth component filtering the stored notes based on the identified filter(s) and rendering the filtered notes based on at least one category.

Figures 1A, 1B:
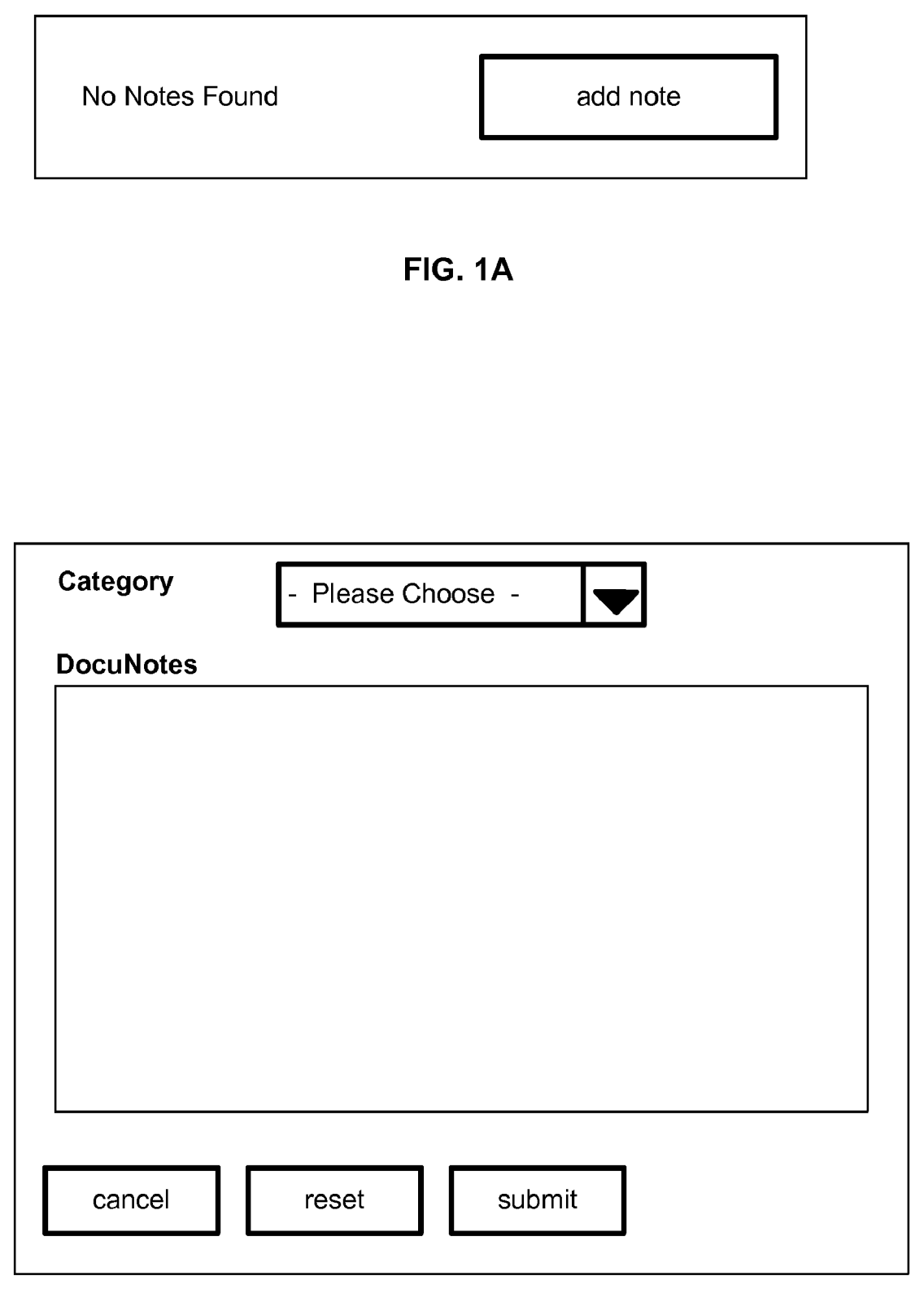

FIGS. 1a-b illustrate an example of how a first note is added as per the present invention. First, in FIG. 1a, a user clicks on an 'add note' button and, in FIG. 1b, the user selects a note category from the category drop down list. The user, then, enters notes in the text box. Once the text is entered, the user clicks the 'submit' button or a tab to the button and presses Enter. Clicking the reset key deletes the text the user entered. If the user does not wish to make a change, the user clicks the 'cancel' button. FIG. 2 Example of a saved note created as per the present invention.

FIG. 2 illustrates the process of adding a new note according to the present invention. First, the user clicks on the 'add new entry' button. Next, the user enters notes in the text box area. After entering the text, the user clicks the 'submit' button. Alternatively, the user can click reset to delete the text entered, or, if the user does not wish to make a change, the user clicks the 'cancel' button. In one embodiment, one may use the outside scroll bar to view previous notes while entering a new note.

All notes that were previously created appear in the Diaries section as shown in FIG. 2. As shown in FIG. 2, the most recent note entered is at the top of the list. To view more notes, the user can scroll down the page.

It should be noted that all new notes are assigned a category (e.g., adjustor, medical management, recovery, SIU, and supervisory) by the person entering the note. It is also possible to assign a "No Category" affiliation to a note.

FIG. 3 illustrates a non-exhaustive list of the various categories that a user can choose from. To view notes for a specific category, users clicks the box next to the category or categories of notes (in the Category Filter section) they need to view (e.g., Adjustor). Pressing the filter button allows the notes to be filtered based on the selected category or categories.

In one embodiment, notes may be edited or deleted within a pre-set time period (e.g., 72 hours) after they are entered. To edit, the user clicks the 'edit' button next to the note you need to edit and the user is able to edit the note as necessary. After editing the text, the user clicks the 'submit' button. Users are also able to delete a note. In an extended embodiment, once a note is deleted, it cannot be restored. After the pre-set time period has passed, the notes are not editable and cannot be deleted as they are stored in non-editable form in a database for historical archival.

The following must be completed for each new note:
Category
Diary text

Every note entry includes the name of the user who added the note and the date the note was created. As mentioned above, in one embodiment, the notes are editable and can be deleted for a pre-set period of time (e.g., notes cannot be deleted or edited more than 72 hours after they are added), after which the notes are not editable and cannot be deleted as they are stored in non-editable form for historical archival. In an extended embodiment, once a note is deleted, it cannot be restored. Text may be copied and pasted into a new Note. It should be noted that a user cannot perform an insert operation without selecting a category.

The present invention also provides for a set of interfaces receiving note submissions and rendering notes based on one or more filters. The interfaces comprises: a first interface to submit notes as formatted text regarding an insurance policy or claim, wherein the notes, after submission, are locked and stored in non-editable form in a database for historical archival; a second interface to select one or more filters, wherein each of the filters allow categorization of the stored locked and non-editable notes based on a set of categories; and a third interface to render, based on a selection of at least one filter, categorized notes based on a set of categories corresponding to said at least one selected filter The present invention also provides for a set of interfaces receiving note submissions and rendering notes based on one or more filters. The interfaces comprises: a first interface to submit notes as formatted text regarding an insurance policy or claim, wherein the notes, after submission, are editable only for a pre-set time period and after the expiration of the pre-set time period, the notes are locked and stored in non-editable form in a database for historical archival; a second interface to select one or more filters, wherein each of the filters allow categorization of the stored locked and non-editable notes based on a set of categories; and a third interface to render, based on a selection of at least one filter, categorized notes based on a set of categories corresponding to said at least one selected filter Additionally, the present invention provides for an article of manufacture comprising computer readable program code contained within implementing one or more modules to implement a computer-implemented electronic diary for entry of notes on an insurance policy or claim. Furthermore, the present invention includes a computer program code-based product, which is a storage medium having program code stored therein which can be used to instruct a computer to perform any of the methods associated with the present invention. The computer storage medium includes any of, but is not limited to, the following: CD-ROM, DVD, magnetic tape, optical disc, hard drive, floppy disk, ferroelectric memory, flash memory, ferromagnetic memory, optical storage, charge coupled devices, magnetic or optical cards, smart cards, EEPROM, EPROM, RAM, ROM, DRAM, SRAM, SDRAM, or any other appropriate static or dynamic memory or data storage devices.

Implemented in computer program code based products are software modules for: aiding in receiving submitted notes as formatted text regarding said insurance policy or claim; aiding in storing said input notes in a database wherein said stored text, after said submission, is non-editable and is locked in said database for historical archival; implementing one or more filters, each of said filters categorizing said notes based on a set of categories; aiding in receiving inputs identifying at least one filter; and filtering said stored notes based on said identified at least one filter and rendering said filtered notes.

Although the above description provides examples of how the present invention's computer-implemented electronic diary to enter locked notes for historical archival is used in the insurance industry, it should be noted that the scope of the invention extends beyond the insurance industry. For example, the electronic diary to enter locked noted for historical archival can be efficiently used in the medical and legal industries. Hence, the specific industry where the present ivnention's electronic diary is used should not be used to limit the scope of the present invention.

CONCLUSION

A system and method has been shown in the above embodiments for the effective implementation of a computer-implemented electronic diary for entry of legal notes. While various preferred embodiments have been shown and described, it will be understood that there is no intent to limit the invention by such disclosure, but rather, it is intended to cover all modifications falling within the spirit and scope of the invention, as defined in the appended claims. For example, the present invention should not be limited by software/program, computing environment, specific computing hardware, or the type of industry (i.e., equally applicable to the other industries).

The above enhancements are implemented in various computing environments. For example, the present invention may be implemented on a conventional PC or equivalent, multinodal system (e.g., LAN) or networking system (e.g., Internet, WWW, wireless web). All programming and data related thereto are stored in computer memory, static or dynamic, and may be retrieved by the user in any of: conventional computer storage, display (i.e., CRT) and/or hardcopy (i.e., printed) formats. The programming of the present invention may be implemented by one of skill in the art of database programming.

The invention claimed is:

1. An article of manufacture having computer readable storage medium having instructions executable by a processor to implement an electronic diary for entry and category-based viewing of legal notes, said method implemented by a processor comprising:

executing instructions to receive legal notes input as formatted text;

executing instructions to store said input legal notes in a database, said stored text, after said submission, are editable for a pre-determined time period and, after expiration of said pre-determined time period, said submission is non-editable and is locked in said database for historical archival;

executing instructions to implement one or more filters, each of said filters categorizing said stored legal notes based on a set of categories;

executing instructions to receive inputs identifying at least one filter;

executing instructions to filter said stored legal notes based on said identified at least one filter; and executing instructions to output categorized legal notes corresponding to said identified filters.

2. The article of manufacture of claim 1, wherein said electronic diary is accessible over a network.

3. The article of manufacture of claim 2, wherein said network is any of the following: local area network, wide area network, or the Internet.

4. A system comprising:

a processor; and a computer readable storage medium having instructions executable by a processor to implement an electronic diary for entry and category-based viewing of legal notes, said processor:

executing instructions to receive legal notes input as formatted text;

executing instructions to store said input legal notes in a database, said stored text, after said submission, are editable for a pre-determined time period and, after expiration of said pre-determined time period, said submission is non-editable and is locked in said database for historical archival;

executing instructions to implement one or more filters, each of said filters categorizing said stored legal notes based on a set of categories;

executing instructions to receive inputs identifying at least one filter;

executing instructions to filter said stored legal notes based on said identified at least one filter; and executing instructions to output categorized legal notes corresponding to said identified filters.

5. The system of claim 4, wherein said electronic diary is accessible over a network.

6. The system of claim 5, wherein said network is any of the following local area network, wide area network, or the Internet.

* * * * *